(12) United States Patent
Liu et al.

(10) Patent No.: US 8,421,035 B2
(45) Date of Patent: Apr. 16, 2013

(54) HIGH-RESOLUTION MICROSCOPE USING OPTICAL AMPLIFICATION

(75) Inventors: Jia-Ming Liu, Los Angeles, CA (US); Enrico Stefani, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 631 days.

(21) Appl. No.: 12/376,853

(22) PCT Filed: Aug. 7, 2007

(86) PCT No.: PCT/US2007/075383
§ 371 (c)(1),
(2), (4) Date: May 25, 2010

(87) PCT Pub. No.: WO2008/021834
PCT Pub. Date: Feb. 21, 2008

(65) Prior Publication Data
US 2010/0276608 A1    Nov. 4, 2010

Related U.S. Application Data

(60) Provisional application No. 60/822,178, filed on Aug. 11, 2006.

(51) Int. Cl.
*G01N 21/64* (2006.01)
(52) U.S. Cl.
USPC .................................................. 250/459.1
(58) Field of Classification Search .............. 250/459.1, 250/458.1
See application file for complete search history.

(56) References Cited

U.S. PATENT DOCUMENTS

| | | | |
|---|---|---|---|
| 4,199,686 A | 4/1980 | Brunsting et al. | |
| 5,608,519 A | 3/1997 | Gourley et al. | |
| 6,177,990 B1 * | 1/2001 | Kain et al. | 356/246 |
| 2003/0011881 A1 * | 1/2003 | Sure | 359/388 |
| 2004/0207854 A1 | 10/2004 | Hell et al. | |
| 2004/0252380 A1 * | 12/2004 | Kashima | 359/656 |
| 2006/0033987 A1 * | 2/2006 | Stelzer et al. | 359/385 |
| 2007/0023686 A1 * | 2/2007 | Wolleschensky et al. | 250/458.1 |

OTHER PUBLICATIONS

Buechler et al., "Time-resolved polarization imaging by pump-probe (stimulated emission) fluorescence microscopy," 2000, Biophysical Jouranl, vol. 79, pp. 536-549.*
International Search Report mailed on Aug. 11, 2008, for International Application No. PCT/US07/75383, 6 pages.

* cited by examiner

*Primary Examiner* — Kiho Kim
(74) *Attorney, Agent, or Firm* — Kilpatrick Townsend and Stockton LLP

(57) ABSTRACT

Systems and methods that enhance the resolution of a microscope in all three spatial dimensions. A microscope system is provided that typically includes a first objective lens (20), an illumination source that provides excitation illumination ($\lambda$ex) at a first wavelength through the objective lens (20) in a first direction onto a fluorescent sample so as to induce fluorescent emission in the sample at a second wavelength ($\lambda$fl) different than the first wavelength. The system also typically includes an element (60) that provides illumination at the second wavelength ($\lambda$fl) to the sample in a second direction different from the first direction, and a detector (10) for detecting the fluorescent emission. The optical gain of the fluorescent emission at the second wavelength is enhanced through stimulated emission.

26 Claims, 2 Drawing Sheets

HIGH-RESOLUTION MICROSCOPE USING OPTICAL AMPLIFICATION

CROSS-REFERENCES TO RELATED APPLICATIONS

This application is a non-provisional application of, and claims priority to, U.S. Provisional Application Ser. No. 60/822,178, filed Aug. 11, 2006, which is hereby incorporated by reference in its entirety.

BACKGROUND

The present invention relates generally to imaging systems and methods, and more particularly to high resolution microscopy systems and methods using optical amplification.

For over a century the resolution of far-field optical microscopes has been limited by the Abbe diffraction limit. This limit applies to both wide-field and laser-scanning microscopes. For the best of current-generation far-field optical microscopes, the resolution limit is around 200 nm in the lateral x and y directions (perpendicular to the beam path) and about 500 nm in the axial z direction (along the beam path). The axial resolution in the z direction is worse than the transverse resolution limit because of the diffraction of the light beam crossing the objective lens. Near-field optical microscopy can reach a lateral resolution better than 100 nm, but it is confined to imaging a surface within the vicinity of the evanescent optical near field. Thus, far-field optical microscopes remain a good option for imaging many 3D structures.

A laser-scanning confocal microscope has the ability to generate 3D images through high-resolution axial sectioning. Such a microscope has a much better depth range than a wide-field microscope of the same resolution, but conventional confocal microscopes are also limited by the Abbe diffraction limit.

A 4 Pi confocal microscope provides an improved resolution in the z direction over that of a conventional confocal microscope by focusing the light with two opposing high numerical aperture (NA) objective lenses to create two interfering spherical waves, which result in a spherical spot (see, e.g., S. Hell and E. H. K. Stelzer, "Properties of a 4 Pi confocal fluorescence microscope," *J. Opt. Soc. Am. A* 9, 2159-2166 (1992)). Even with this improvement, the resolution of a 4 Pi microscope is also diffraction-limited.

Nonlinear techniques can break the diffraction limit. Recently, it was demonstrated that it is possible to narrow the focal spot of a fluorescence microscope below the diffraction limit by applying the highly nonlinear process of stimulated emission, a technique known as stimulated emission depletion (STED) (see, e.g., T. A. Klar, S. Jakobs, M. Dyba, A. Egner, and S. W. Hell, "Fluorescence microscopy with diffraction resolution barrier broken by stimulated emission," *Proc. Arad Acad. Sci.* 97, 8206-8210 (2000)). In STED techniques, a long-wavelength de-excitation pulse follows immediately after a short-wavelength excitation pulse. The de-excitation pulse contains a zero in its spatial intensity profile at the beam center and is aligned around the excitation focal point in a ring structure so that the molecules in the center of the ring are excluded from de-excitation. Saturation depletion by the de-excitation pulse dramatically reduces the fluorescent spot in the center to a transverse subdiffraction size that is not limited by the wavelength, but only by the applicable pulse intensity. A transverse resolution down to 16 nm in the focal plane, corresponding to about 1/50 of the STED wavelength of 775 nm was recently accomplished (see V. Westphal and S. W. Hell, "Nanoscale resolution in the focal plane of an optical microscope," *Phys. Rev. Lett.* 94, 143903 (2005)). If conventional confocal imaging is used for a STED microscope, however, the axial resolution in the z direction is still limited to about ½ of the wavelength.

A combination of STED with 4 Pi microscopy has lead to a resolution of 30-50 nm in the z direction (see, e.g., M. Dyba and S. W. Hell, "Focal spots of size $\lambda/23$ open up far-field fluorescence microscopy at 33 nm axial resolution," *Phys. Rev. Lett.* 88, 163901 (2002)). However, existing 4 Pi schemes, which use two opposing high NA objective lenses that focus at the same spot, are expensive and very difficult to align. Also, STED requires the use of two ultrashort (e.g., picosecond or femtosecond) laser pulses, one at the excitation wavelength and another at the STED wavelength. The pulses have to be synchronized for the STED pulse to follow the excitation pulse at an optimum delay, and the spatial phase of the STED pulse has to be manipulated through special optics so that it is focused into a spatial profile that has a zero at the center. Furthermore, the focused STED pulse has to be carefully aligned with the excitation pulse so that the zero at its center overlaps with the peak of the excitation spot exactly at nanometer resolution. As a consequence, STED is also very expensive and difficult to implement.

Therefore it is desirable to provide systems and methods that overcome the above and other problems.

BRIEF SUMMARY

The present invention provides systems and methods that enhance the resolution of a microscope in all three spatial dimensions. The present invention is particularly useful in a microscope, or any imaging instrument, that functions on the principle of fluorescence emission by excitation of a focused light source. Examples include, but are not limited to, laser scanning fluorescence microscopes, fluorescence confocal microscopes, two-photon fluorescence microscopes, and microscopic photoluminescence imaging systems.

According to one aspect of the present invention, a microscope system is provided that typically includes a first objective lens, an illumination source that provides excitation illumination at a first wavelength through the objective lens in a first direction onto a fluorescent sample so as to induce fluorescent emission in the sample at a second wavelength different than the first wavelength. The system also typically includes an element that provides illumination at the second wavelength to the sample in a second direction different from the first direction, and a detector for detecting the fluorescent emission, wherein an optical gain of the fluorescent emission at the second wavelength is enhanced through stimulated emission. In certain aspects the second direction is opposite the first direction. In certain aspects, the second wavelength is longer than the first wavelength. In certain aspects, the second wavelength is shorter than the first wavelength.

According to another aspect of the present invention, a method is provided for enhancing resolution in a fluorescence microscope. The method typically includes illuminating a fluorescent sample from a first direction with an excitation beam having a first wavelength so as to induce fluorescent emission in the sample at a second wavelength different than the first wavelength, providing illumination light at said second wavelength to said sample from a second direction different from the first direction, and detecting the fluorescent emission, wherein an optical gain of the fluorescent emission at the second wavelength is enhanced through stimulated emission. In certain aspects the second direction is opposite the first direction. In certain aspects, the second wavelength is longer than the first wavelength. In certain aspects, the second wavelength is shorter than the first wavelength.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION OF THE INVENTION

Figures 1, 2, 3:
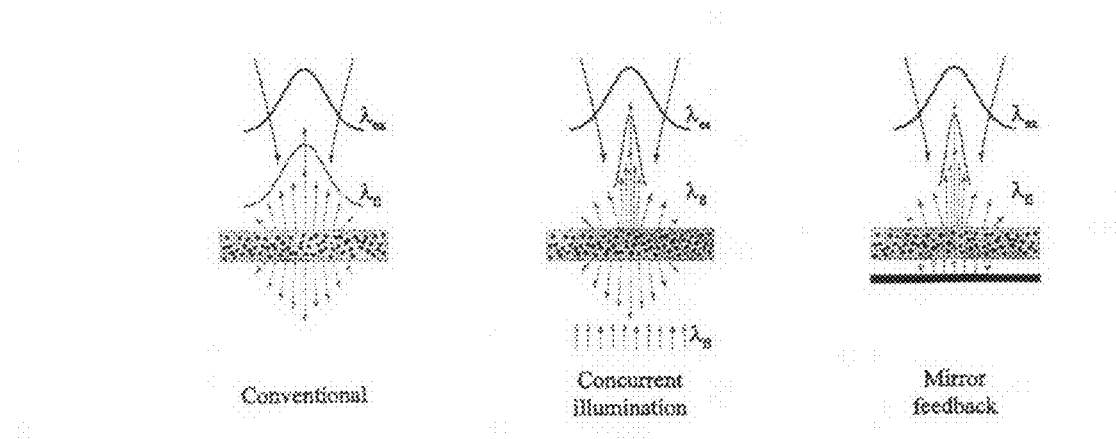
FIG. 1 illustrates the basic concepts of conventional fluorescence microscopy.
FIG. 2 illustrates optical amplification fluorescence microscopy with concurrent illumination according to one embodiment.
FIG. 3 illustrates optical amplification fluorescence microscopy with mirror feedback according to one embodiment.

The present invention provides systems and methods that use optical amplification to enhance the resolution of a fluorescent or luminescent emitting region such as a spot on a sample. In conventional fluorescence microscopy, the emitted fluorescence is linearly proportional to the local intensity of the illumination light (when avoiding the saturation or bleaching of the fluorophores). Thus, the fluorescence spot size is determined by the focused illumination beam spot size, which is limited by the Abbe diffraction limit.

Embodiments of the present invention overcome this limitation by using the process of optical amplification of the fluorescence wavelength through the optical gain provided by the illuminated fluorophores. A fluorophore, such as a fluorescent dye or a quantum dot, is generally a quasi-two-level or four-level system, not a three-level system, i.e., the lower energy level of its fluorescence transition lies above its ground level from which optical excitation by illumination takes place. Therefore, illuminated fluorophores have a population inversion with an optical gain for the fluorescence emission. If no light at the fluorescence wavelength is present to induce stimulated emission, the fluorophores will spontaneously relax to emit spontaneous photons, as in the case of conventional fluorescence microscopy. In this situation, the emitted fluorescence is linearly proportional to the excited population, which in turn is proportional to the local intensity of the illumination light if the fluorophores are not saturated or bleached. This is the situation in conventional fluorescence microscopy as shown in FIG. 1, where $\lambda_{ex}$ is the excitation or illumination light and $\lambda_{fl}$ is the fluorescent emission light.

According to one embodiment, light at the fluorescence wavelength is provided to the fluorescing fluorophores, such as through feedback or through concurrent low-level illumination of the illuminated spot. If light at the fluorescence wavelength $\lambda_{fl}$ is present while the fluorophores are illuminated (at the excitation wavelength $\lambda_{ex}$), the optical gain provided by the illuminated fluorophores is amplified through stimulated emission. The intensity of the amplified light grows exponentially, not linearly, with the optical gain. Thus, the amplified intensity is not proportional to, but varies exponentially with, the local intensity of the illumination light. Consequently, the total emission, including spontaneous emission, feedback or additional illumination, and amplified emission, at the fluorescence wavelength has a much sharper spatial profile in three dimensions than that of the focused illumination spot if the amplified emission is stronger than the rest of the emission. Because this is a highly nonlinear process, the emission profile can continue to be sharpened far beyond the Abbe diffraction limit until saturation or bleaching of the fluorophores occurs. Furthermore, the total emission collected by the microscope objective at the fluorescence wavelength is significantly increased by this process, thus enhancing the contrast of the microscope.

FIG. 2 shows optical amplification fluorescence microscopy with concurrent illumination according to one embodiment. As shown, a second illumination source provides concurrent illumination of the fluorescing region at the fluorescent wavelength $\lambda_{fl}$. The second source, in this embodiment, can include a second laser tuned to the fluorescent wavelength or another illumination source that emits light including a component at the fluorescent wavelength. Useful illumination sources include lasers, light-emitting diodes and white light sources. In certain aspects, the illumination beam at the excitation wavelength is more intense than the back illumination beam at the fluorescence wavelength. For example, in one aspect, the specimen is concurrently back-illuminated with the low-intensity light at the fluorescence wavelength while the specimen is illuminated by a focused, strong illumination beam at the excitation wavelength. In this manner, the backward propagating low-intensity light at the fluorescence wavelength serves as the seed to induce stimulated emission in the illuminated fluorophores. Both the back-emitted fluorescence and the amplified light at the fluorescence wavelength are collected by an objective lens.

FIG. 3 shows optical amplification fluorescence microscopy with reflection (e.g., mirror) feedback according to one embodiment. As shown, a reflecting element, such as a mirror, reflects emitted fluorescence back through the emitting fluorophores. In this embodiment, the source of the concurrent illumination at the fluorescing wavelength includes the emitted fluorescence itself.

The above discussion, and FIGS. 2 and 3, are described and illustrated in terms of a one-photon excitation process. However, aspects of the present invention are also applicable to two-photon fluorescence microscopy, in which the excitation is a two-photon process.

Figure 4:
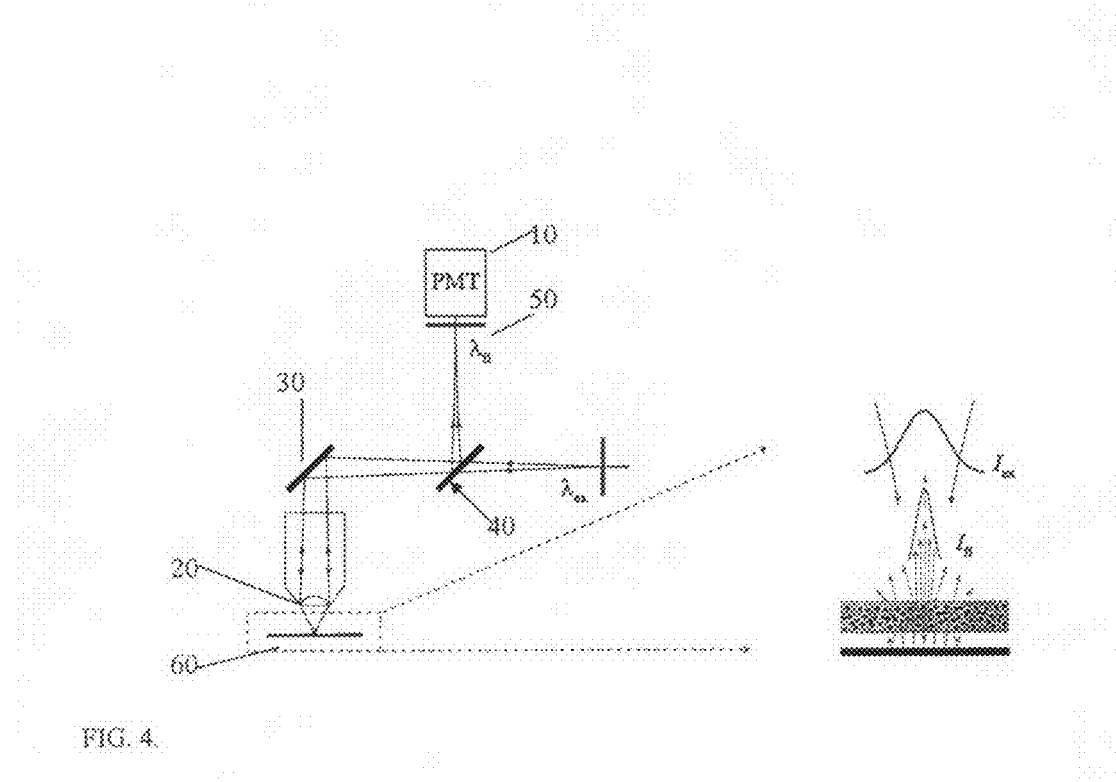
FIG. 4 illustrates a schematic structure of a confocal fluorescence microscope using a reflecting mirror (hereinafter "Reflexion Confocal Microscope") according to one embodiment.

Embodiments of the present invention can be implemented in any fluorescence microscope by, for example, placing the specimen directly on a mirror element, such as a totally reflecting mirror, and/or by providing back illumination at the fluorescing wavelength from a second illumination source. FIG. 4 shows the schematic structure of a confocal fluorescence microscope using a reflecting mirror according to one embodiment. This configuration is termed a "Reflexion Confocal Microscope". The mirror element 60 can be either flat or curved, e.g., concave. In this manner, any forward-emitted fluorescence reflected by the mirror 60 is amplified by the excited fluorophores in its return pass through the fluorophores. Both the initially back-emitted fluorescence and the amplified fluorescence are collected using an objective lens 20. For example, in one embodiment as shown in FIG. 4, a detector element 10 receives the fluorescent light. Optical elements such as mirror 30 and mirror 40 may be used to direct the light toward the detector element 10. For example, mirror element 40 redirects light at the fluorescent wavelength toward the detector 10 and simultaneously allows light at the excitation wavelength to pass. A pinhole 50 placed in front of the detector 10 provides a confocal microscope arrangement in conjunction with objective lens 20 according to one aspect. Examples of useful detector elements include photomultiplier tubes (PMTs) and avalanche photodiodes (APDs). The arrangement of FIG. 4 can also have the added function of a 4 Pi microscope to further enhance the resolution in the z direction without the need of using two opposing high NA objective lens if the specimen and the mirror are properly placed.

In certain aspects, the present invention can be practiced with two-photon excitation as in a two-photon fluorescence microscope. In this case, the excitation beam has a wavelength that is twice that of the one-photon excitation wavelength, thus a photon energy that is half that of the one-photon excitation. Optical feedback using a reflecting mirror element and/or concurrent back-illumination using a second illumination source at the fluorescence wavelength as described herein can be employed. In the case of two-photon absorption, the emitted fluorescence may have a wavelength that is shorter than the excitation wavelength.

Advantages

The present invention can advantageously be implemented on any fluorescence microscope, confocal or nonconfocal, to significantly enhance the resolution of the microscope in all three (x, y, and z) dimensions.

The cost of implementing aspects of the present invention are negligible compared to the costs of a microscope. In other words, aspects of the present invention provide an increase of resolution by many folds with almost no overhead to any existing fluorescence microscope.

Systems and methods of the present invention significantly reduce the axial z resolution and break the Abbe diffraction limit. For example, existing 4 Pi schemes, which use two opposing high NA objective lenses that focus at the same spot, are expensive and very difficult to align. The present invention has minimum cost overhead and no special requirement on optical alignment. Furthermore, 4 Pi does not break the diffraction limit and does not improve lateral resolution (in x and y). The present invention can break the diffraction limit in all three dimensions.

Aspects of the present invention do not have any of the special requirements of STED. For example, in certain aspects, a single inexpensive CW light source may be used that does not require special temporal synchronization or spatial alignment. In STED, the collected fluorescence decreases with the increase in the resolution; thus its contrast decreases as the resolution increases. For the present invention, the collected light intensity at the fluorescence wavelength increases with the increases in resolution through the amplification process, as mentioned above. Thus, the contrast increases with resolution. Additionally, STED has only been shown to work with fluorescent dyes, which has very broad fluorescence emission spectra. It has never been shown to work with quantum dots, which have relatively narrow fluorescence emission spectra. Indeed, its principle requires that the STED transition and the fluorescence transition use different transition levels, thus prohibiting its functioning on fluorophores that have a pair of narrow emission transition levels. Systems and methods of the present invention are not limited by any of these requirements; they have been shown to work with both quantum dots and fluorescence dyes, and will work with any material that can have an optical gain while being excited.

The systems and methods of the present invention provide a significant breakthrough in the resolution of fluorescence microscopy, and have already shown to reach a subdiffraction resolution in all three dimensions, and have also been used to take images of cellular structures with many-fold increase in resolution over a commercial confocal microscope. Today, fluorescence microscopy is an important technology for research in biology and medicine.

According to one aspect of the present invention, microscopic slides and coverslips fabricated with a mirror layer are provided for use with the embodiments of the present invention.

EXAMPLES

Figure 5:
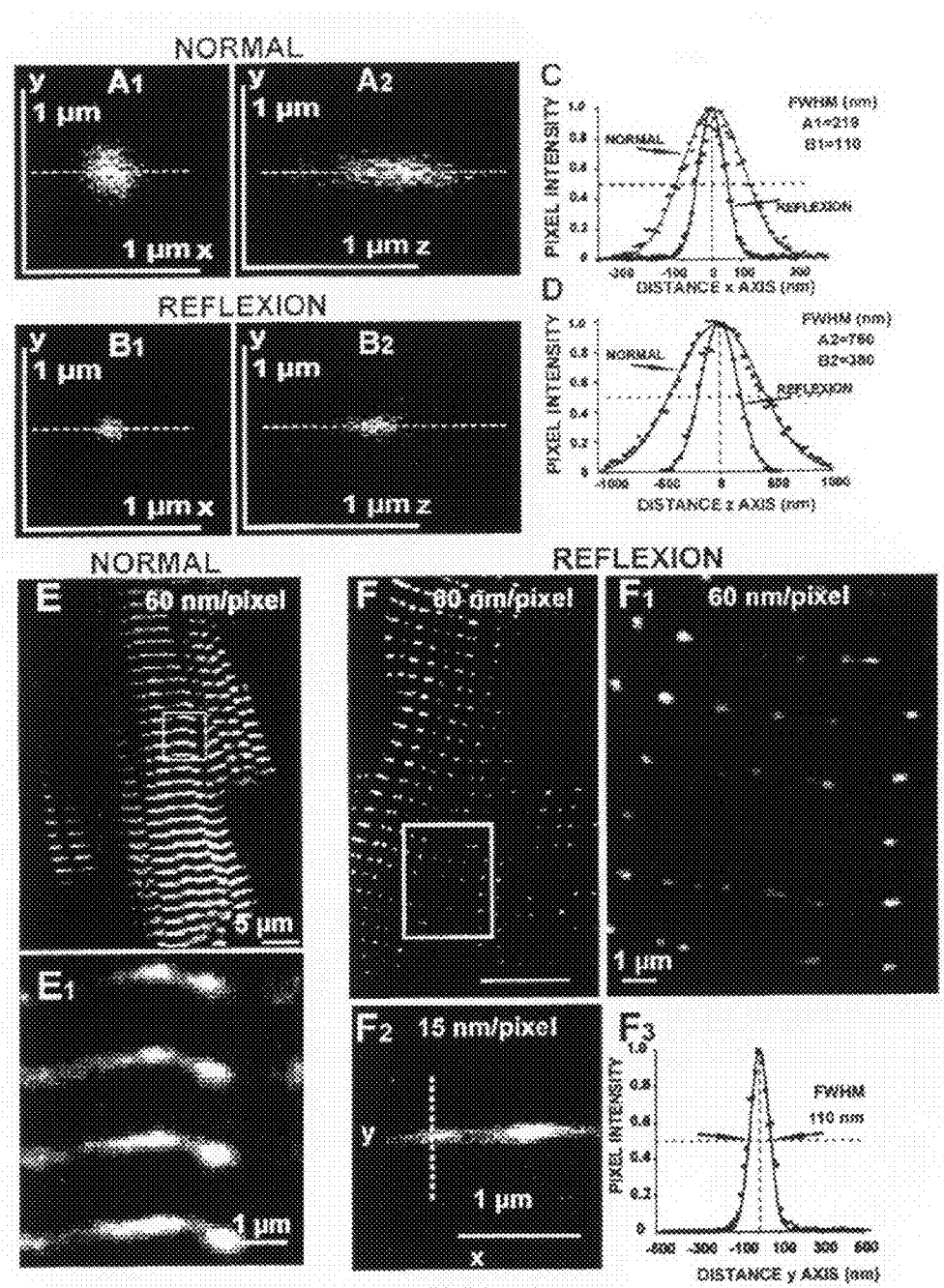
FIG. 5 illustrates improved x, y, z resolution using embodiments of the present invention.

FIG. 5 illustrates improved x, y, z resolution using the systems and methods of the present invention. FIG. 5(A,B) show a point spread function (PSF) in x,y (A1,B1) and y,z (A2,B2) planes from ~10 nm quantum dots excited at 405 nm (CW laser) and the emission recorded at 545 nm in a confocal microscope (A) and after converting it to a Reflexion Confocal Microscope by the addition of the reflexion mirror (B). FIG. 5 (C,D) show a pixel intensity line scan along the x axis (C, dashed lines in A1,B1) and along the z axis (D, dashed lines in A2,B2). In the normal confocal microscope, values of full-width-at-half-maximum (FWHM) are 219 nm in the x,y plane and 760 nm in the z direction. These values are close to the theoretical diffraction limit ($\Delta x; \Delta y=168$ nm; $\Delta z=723$ nm), from $\Delta x; \Delta y=\lambda/2n \sin \alpha$ and $\Delta z=2\lambda/(n \sin 2\alpha)$, where $\lambda$, n and $\alpha$ are the wavelength, the refractive index, and the semiaperture angle of the objective lens, respectively. In the reflexion confocal microscope FWHM values ($\Delta x$, $\Delta y=110$ nm; $\Delta z=380$ nm) were smaller than the ones expected for the diffraction limit. The sampling rate was 10 nm/pixel in the xy plane and 40 nm/plane in the z axis. FIG. 5 (E) shows a single optical section with the normal confocal microscope of a heart cardiomyocyte tagged with anti-α-actinin antibody which was labeled with Alexa 405 secondary antibody. The fluorophore was excited at 405 nm and its emission recorded at 525 nm. The figure illustrates the distribution of α-actinin along the Z line. FIG. 5 (E1) shows a blow up of the square in (E). FIG. 5 (F-F2) show the same conditions as in (E), but with the reflexion mirror included. The images show with higher definition the clustering pattern of α-actinin. FIG. 5 (F3) Pixel intensity line scan along the y axis of an α-actinin cluster (dashed line in F2) of the same cell in (F) at a higher sampling rate. The line scan in (F3) shows FWHM=110 nm which is below the diffraction limit demonstrating the higher resolution of the Reflexion Microscope in biological samples. Images were acquired with a ×100 1.4 NA plan achromate objective lens (Zeiss).

While the invention has been described by way of example and in terms of the specific embodiments, it is to be understood that the invention is not limited to the disclosed embodiments. To the contrary, it is intended to cover various modifications and similar arrangements as would be apparent to those skilled in the art. For example, the back illumination at the fluorescence wavelength may illuminate the sample from any direction or angle, e.g., from the side at 90 degrees relative to the excitation illumination. Therefore, the scope of the appended claims should be accorded the broadest interpretation so as to encompass all such modifications and similar arrangements.

What is claimed is:

1. A method of enhancing resolution in a fluorescence microscope, the method comprising:

illuminating a fluorescent sample from a first direction with an excitation beam having a first wavelength so as to induce fluorescent emission in the sample at a second wavelength different than the first wavelength;

reflecting, using a mirror element, a portion of the fluorescent emission at said second wavelength back to said sample from a second direction different from the first direction, causing enhanced optical gain of the induced fluorescent emission in the sample through stimulated emission; and detecting the fluorescent emission.

2. The method of claim 1, wherein the mirror element is substantially flat.

3. The method of claim 1, wherein the mirror element is curved.

4. The method of claim 1, wherein the first wavelength is twice the one-photon absorption wavelength of the fluorescent sample.

5. The method of claim 1, wherein the intensity of the detected fluorescent emission varies exponentially with the intensity of the excitation illumination.

6. The method of claim 1, wherein the fluorescence microscope is a confocal microscope.

7. The method of claim 1, wherein the fluorescence microscope is a non-confocal microscope.

8. The method of claim 1, wherein the second wavelength is longer than the first wavelength.

9. The method of claim 1, wherein the second wavelength is shorter than the first wavelength.

10. The method of claim 1, wherein the second direction is opposite the first direction.

11. The method of claim 1, wherein the excitation beam having a first wavelength is continuous wave (CW).

12. A microscope system, comprising:
a first objective lens;
an illumination source that provides excitation illumination at a first wavelength through the objective lens in a first direction onto a fluorescent sample so as to induce fluorescent emission in the sample at a second wavelength different than the first wavelength;
a mirror that reflects a portion of the fluorescent emission at the second wavelength back to the sample in a second direction different from the first direction, causing enhanced optical gain of the fluorescent emission in the sample at the second wavelength through stimulated emission; and
a detector for detecting the fluorescent emission.

13. The microscope system of claim 12, wherein the mirror is substantially flat.

14. The microscope system of claim 12, wherein the mirror is substantially flat and is attached to a slide or platform on which the sample resides.

15. The microscope system of claim 12, wherein the mirror is curved.

16. The microscope system of claim 12, wherein the first wavelength is twice the one-photon excitation wavelength of the fluorescent sample.

17. The microscope system of claim 12, wherein the intensity of the detected fluorescent emission varies exponentially with the intensity of the excitation illumination.

18. The microscope system of claim 12, wherein the fluorescence microscope is a confocal microscope.

19. The microscope system of claim 12, wherein the fluorescence microscope is a 4Pi microscope that includes a second objective lens positioned on the side of the sample opposite the first objective lens.

20. The system of claim 12, wherein the second direction is opposite the first direction.

21. The system of claim 12, wherein the fluorescence microscope is a non-confocal microscope.

22. The system of claim 12, wherein the second wavelength is longer than the first wavelength.

23. The system of claim 12, wherein the second wavelength is shorter than the first wavelength.

24. The system of claim 12, wherein the illumination source that provides excitation illumination at a first wavelength is a continuous wave (CW) light source.

25. A microscope system, comprising:
a first objective lens;
an illumination source that provides peak excitation intensity at a first wavelength through the objective lens in a first direction onto a point on a fluorescent sample so as to induce fluorescent emission in the sample at a second wavelength different than the first wavelength;
an element that provides peak illumination intensity at the second wavelength onto the point on the sample in a second direction different from the first direction, causing enhanced optical gain of the fluorescent emission in the sample at the second wavelength through stimulated emission; and
a detector for detecting the fluorescent emission.

26. The system of claim 25, wherein the illumination source that provides excitation intensity at a first wavelength is a continuous wave (CW) light source.

* * * * *